United States Patent [19]

Geerlandt et al.

[11] Patent Number: 5,750,684

[45] Date of Patent: May 12, 1998

[54] PROCESS FOR THE PREPARATIN OF β-LACTAM COMPOUNDS

[75] Inventors: Hervé Geerlandt, Bruxelles; Claudine Grand'Henry, Ohain, both of Belgium

[73] Assignee: Beecham Group plc., Middlesex, England

[21] Appl. No.: 758,433

[22] Filed: Aug. 30, 1991

Related U.S. Application Data

[63] Continuation of Ser. No. 622,329, Nov. 27, 1990, abandoned, which is a continuation of Ser. No. 422,121, Oct. 16, 1989, abandoned, which is a continuation of Ser. No. 134,216, Dec. 17, 1987, abandoned, which is a continuation of Ser. No. 560,444, Dec. 12, 1983, abandoned.

[30] Foreign Application Priority Data

Dec. 14, 1982 [GB] United Kingdom ............ 8235568

[51] Int. Cl.$^6$ ................................................ C07D 499/04

[52] U.S. Cl. ................ 540/319; 540/205; 540/221; 540/301

[58] Field of Search ........................... 540/221, 315, 540/205, 301, 319

[56] References Cited

U.S. PATENT DOCUMENTS 4,447,602   5/1984   Firestone et al. ............... 540/312

FOREIGN PATENT DOCUMENTS

| | | |
|---|---|---|
| 1040620 | 10/1978 | Canada. |
| 1401059 | 7/1975 | United Kingdom. |
| 1412886 | 11/1975 | United Kingdom. |
| 1463468 | 2/1977 | United Kingdom. |
| 1576796 | 10/1980 | United Kingdom. |

OTHER PUBLICATIONS

*The Journal of Organic Chemistry*, vol. 38, No. 7, pp. 1436–1437, Apr. 6, 1973.

*Journal of the American Chemical Society*, vol. 95, No. 7, pp. 2403–2404, Apr. 4, 1973.

Lann et al., *Tetrahedron Letters*, No. 14, pp. 1311–1313, (1974).

*The Journal of Organic Chemistry*, vol. 38, No. 7, Apr. 6, 1973, pp. 1436–1437.

*Journal of the American Chemical Society*, vol. 95, No.7, Apr. 4, 1973, pp. 2403–2404.

W.H.W. Lunn et al.*Tetrahedron Letters*, No. 14, pp. 1311–1313, (1974).

*Primary Examiner*—José G. Dees
*Attorney, Agent, or Firm*—Stephen Venetianer; Edward T. Lentz

[57] ABSTRACT

The present invention provides a process for the substitution of an acylamino β-lactam compound at the carbon atom carrying the acylamino group, which process comprises reacting the β-lactam compound with an halogenating agent and a nucleophilic reagent; characterized in that the acylamino group has an acidic group on the carbon atom adjacent the carbonyl group.

In particular the process of this invention comprises reacting a β-lactam of partial structure (I):

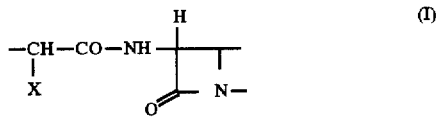

where X represents an acidic group; with an halogenating agent and a nucleophilic reagent.

10 Claims, No Drawings

PROCESS FOR THE PREPARATIN OF β-LACTAM COMPOUNDS

This is a continuation of application Ser. No. 07/622,329 filed Nov. 27, 1990, now abandoned; which is a continuation of application Ser. No. 07/422,121 filed Oct. 16, 1989, abandoned; which is a continuation of application Ser. No. 07/134,216 filed Dec. 17, 1987, abandoned; which is a continuation of application Ser. No. 06/560,444 filed Dec. 12, 1983, abandoned.

This invention relates to a chemical process for the preparation of β-lactam compounds, and in particular for the introduction of a substituent into a β-lactam having an acylamino side chain containing an α-acidic group. Certain of the substituted β-lactam compounds produced by this process are antibacterial agents; others are useful as intermediates for producing such agents.

The present invention provides a process for the substitution of an acylamino β-lactam compound at the carbon atom carrying the acylamino group, which process comprises reacting the β-lactam compound with a halogenating agent and a nucleophilic reagent; characterised in that the acylamino group has an acidic group on the carbon atom adjacent the carbonyl group.

In particular the process of this invention comprises reacting a β-lactam of partial structure (I):

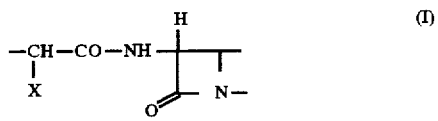

where X represents an acidic group; with an halogenating agent and a nucleophilic reagent.

The acidic group may be, for example a carboxy group, $CO_2H$, or other group which can carry a negative charge such as sulpho or, $SO_3H$.

The acidic group is attached to the carbon atom adjacent to the carbonyl group of the acylamino side chain, which is usually referred to as the alpha position of the side chain.

It is believed that the process of this invention proceeds via attack of the nucleophilic reagent at the position marked * in structure (IA):

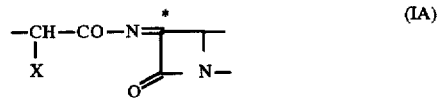

The nucleophilic reagent therefore may represent any source of a nucleophile which is able to undergo this reaction. Examples of such nucleophiles include, for example, alkoxy and alkylthio.

In one aspect, therefore this invention provides a process for the preparation of a β-lactam derivative of partial structure (II):

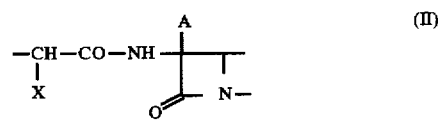

where A represents alkoxy or alkylthio; and X represents an acidic group; which process comprises reacting a β-lactam of partial structure (I) with an halogenating agent and a source of an alkoxy or alkylthio radical.

Suitable alkyl groups in the alkoxy and alkylthio moieties include straight and branched chain alkyl groups containing from 1 to 6 carbon atoms, such as methyl, ethyl, propyl and butyl. A particular alkyl group is methyl.

Preferably A represents alkoxy, suitably $C_{1-6}$ alkoxy.

The partial structure (II) preferably represents a penam, bisnorpenam, cephem or oxacephem.

Thus, in a preferred aspect the present invention provides a process for the preparation of an antibacterially active β-lactam compound of formula (III):

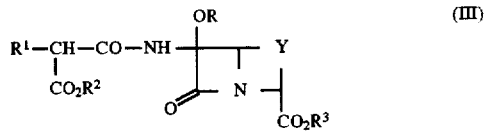

wherein R represents $C_{1-6}$ alkyl, $R^1$ represents a hydrocarbon or heterocyclyl group, $R^2$ represents hydrogen or a pharmaceutically acceptable salt or ester group, $R^3$ represents hydrogen or a pharmaceutically acceptable salt or in vivo hydrolysable ester group, and Y represents —S—C(CH$_3$)$_2$—, —S—CH$_2$—, or —Y$^1$—CH$_2$—C(Z)=, wherein $Y^1$ is oxygen, sulphur or —CH$_2$— and Z represents hydrogen, halogen, $C_{1-6}$ alkoxy, —CH$_2$Q or —CH=CH—Q wherein Q represents hydrogen, halogen, hydroxy, mercapto, cyano, pyridinium, carboxy or ester thereof, $C_{1-6}$ alkoxy, acyloxy, aryl, heterocyclyl or heterocyclylthio; which process comprises reacting a compound of formula (IV):

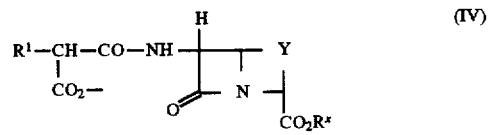

where $R^1$, and Y are as defined with respect to formula (III) and $R^x$ is hydrogen or a carboxyl blocking group; with a halogenating agent and a source of the ion RO—; and optionally thereafter converting the product to a salt or ester.

The term 'hydrocarbon' includes groups having up to 18 carbon atoms, suitably up to 10 carbon atoms, conveniently up to 6 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{5-7}$ cycloalkenyl, $C_{3-7}$ cycloalkyl($C_{1-6}$)-alkyl, aryl, and aryl($C_{1-6}$)alkyl.

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$)alkyl, hydroxy, amino, nitro, carboxy, $C_{1-6}$ alkoxycarbonyl, $C_{1-6}$ alkoxycarbonyl-($C_{1-6}$)-alkyl $C_{1-6}$ alkylcarbonyloxy, or $C_{1-6}$ alkylcarbonyl groups.

The term 'heterocyclyl' includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, optionally substituted amino, optionally substituted amino($C_{1-6}$)alkyl, carboxy, $C_{1-6}$ alkoxycarbonyl, $C_{1-6}$ alkoxycarbonyl($C_{1-6}$)alkyl, carboxy($C_{1-6}$)alkyl, sulpho ($C_{1-6}$)alkyl, aryl or oxo groups.

Suitably the heterocyclic ring comprises from 4 to 7 ring atoms, preferably 5 to 6 atoms.

Preferred values for Y in the compounds of formula (III) are —S—C(CH$_3$)$_2$ and —S—CH$_2$—C(CH$_2$Q)=, i.e. the compound of formula (III) is a derivative of a penicillin or cephalosporin.

A particularly preferred value for Y is —S—C(CH$_3$)$_2$—.

Preferably $R^1$ represents phenyl, p-hydroxyphenyl, 3,4-dihydroxyphenyl, or 2- or 3-thienyl.

Preferably R represents methyl.

Examples of suitable pharmaceutically acceptable in vivo hydrolysable ester groups include those which break down readily in the human body to leave the parent acid or its salt. Suitable ester groups of this type include those of part formula (i), (ii) and (iii):

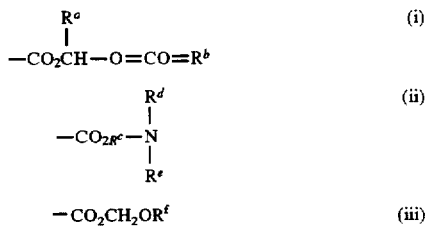

$$-CO_2CH-O=CO=R^b \quad \overset{R^a}{|} \qquad (i)$$

$$-CO_{2R^c}-N \quad \overset{R^d}{\underset{R^e}{|}} \qquad (ii)$$

$$-CO_2CH_2OR^f \qquad (iii)$$

wherein $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups; $R^c$ represents $C_{1-6}$ alkylene optionally substituted with a methyl or ethyl group; $R^d$ and $R^e$ independently represent $C_{1-6}$ alkyl; $R^f$ represents $C_{1-6}$ alkyl. Examples of suitable in vivo hydrolysable ester groups include for example acyloxyalkyl groups such as acetoxymethyl, pivaloyloxymethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

Suitable pharmaceutically acceptable salts of the compounds of formula (III) include metal salts, e.g. aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine, cycloalkylamines such as dicyclohexylamine, or with procaine, dibenzylpiperidine, N-benzyl-β-phenethylamine, dehydroabietylamine, N,N'-bisdehydroabietylamine, ethylenediamine, or bases of the pyridine type such as pyridine, collidine or quinoline.

Suitable carboxyl-blocking derivatives for the group —$CO_2R^x$ in formula (IV) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. Preferred salts are with sodium or triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxy-benzyl, benzoylmethyl, p-bromobenzoylmethyl, p-nitrobenzyl, 4-pyridylmethyl, 2,2,2-trichloroethyl, 2,2,2-tribromoethyl, t-butyl, allyl, acetonyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, an oxime radical of formula —N=$CHR^o$ where $R^o$ is aryl or heterocyclic, or an in vivo hydrolysable ester radical such as defined above.

The carboxyl group may be regenerated from any of the above esters by usual methods appropriate to the particular $R^x$ group, for example, acid- and base-catalysed hydrolysis, or by enzymically-catalysed hydrolysis, or by hydrogenation.

Suitable halogenating agents for the process of the present invention include hypohalite, N-haloamide,N-haloimide, N-halosulphonamide, 1-halobenzotriazole, and halotriazine compounds. Specific examples include methyl hypochlorite, ethyl hypochlorite, isopropyl hypochlorite, t-butyl hypochlorite, t-butylhypoiodite, N-chloroacetamide, N-chlorosuccinimide, N-bromosuccinimide, N-bromophthalimide, N-chlorobenzenesulphonamide, N-chloro-p-toluenesulphonamide, 1-bromobenzotriazole. A preferred agent is t-butyl hypochlorite. When t-butyl hypochlorite is employed, it is preferred that the agent is as pure as possible, preferably distilled or freshly prepared.

The function of the halogenating agent employed in the process of the present invention is to halogenate the nitrogen atom attached to the β-lactam ring. The halogenated intermediate is then dehydrohalogenated to produce the acylimine intermediate of structure (IA). The halogenation reaction is facilitated by a base. It is therefore preferable to employ the halogenating agent in the presence of a strong base. Suitable strong bases include sodium hydride, lithium di-isopropylamide, phenyl lithium and butyl lithium. Alternatively it is convenient to employ as a strong base, a compound which can also provide the desired nucleophilic agent for the process, such as for example an alkali metal alkoxide.

As the halogenation step of the present process to produce the acylimine intermediate (IA) occurs prior to the nucleophilic addition thereto, the order of addition of the reagents to the β-lactam starting material may be the halogenating agent followed by the nucleophilic reagent. However, in order to avoid or reduce unwanted side reactions of the halogenating agent, the nucleophilic reagent may be added first, so that as the halogenating agent is added, the acylimine intermediate (IA) is produced and reacts in situ with the nucleophilic reagent present. This mode of carrying out the reaction is particularly advantageous when the nucleophilic reagent is a strong base and can be used as the base to facilitate the action of the halogenating agent.

The solvent employed in the process of this invention should be an anhydrous solvent in which the starting materials are soluble. Suitable solvents for the process include methanol, ethanol, methylene dichloride, dimethylformamide, dimethacetamide, dimethoxyethane, tetrahydrofuran, dioxan, methyl acetate, ethyl acetate and isopropyl acetate or mixtures of any such solvents.

The process is conveniently carried out at low temperature, suitably less than 0° C. The preferred temperature for a particular reaction will depend on the nature of the β-lactam starting material and the reagents employed.

The process is carried out for a short period, for example up to 60 minutes, conveniently less than 30 minutes, suitably from 3 to 10 minutes. The reaction mixture is then conveniently quenched by acidification.

Suitable acids which may be used to quench the reaction are concentrated mineral acids, such as concentrated sulphuric acid, and low molecular weight alkyl carboxylic acids such as formic acid, acetic acid or propionic acid, optionally in the presence of a tri-alkylphosphite.

The product of the process may be isolated by conventional methods such as solvent extraction, chromatographic separation in particular ion-exchange chromatography, precipitation, freeze-drying and spray-drying techniques.

Suitable solvents for the precipitation of the product include non-polar solvents such as methyl isobutyl ketone, isopropyl ether, methylene dichloride and diethyl ether.

In a further preferred aspect of this invention, there is provided a process for the preparation of an antibacterially active β-lactam derivative of formula (V) or a pharmaceutically acceptable salt thereof:

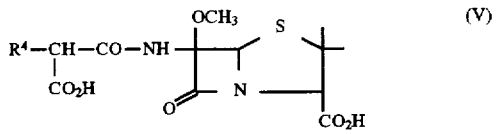

wherein $R^4$ is phenyl, p-hydroxyphenyl or 2- or 3-thienyl; which process comprises reacting a salt of a compound of formula (VI):

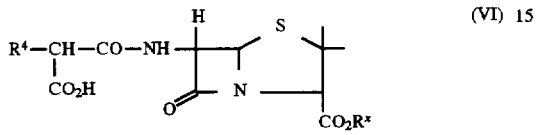

where $R^x$ is a carboxy-blocking group; with a halogenating agent and a source of methoxide ions, $CH_3O$—; and if $R^x$ is other than a salt, converting the group —$CO_2$ $R^x$ to a free acid or salt.

The group $R^4$ in formula (V) and (VI) is preferably phenyl or thienyl, especially 3-thienyl.

In this aspect of the invention, a preferred halogenating agent is again t-butyl hypochlorite. Preferably the methoxide ions are present prior to, or at the same time as, the halogenating agent so that they can act as a base to remove a proton and thereby facilitate the halogenation. Preferably therefore an additional equivalent of methoxide is employed so that it can act as a base and as a nucleophilic reagent.

Suitably the source of methoxide ions is an alkali metal alkoxide such as sodium or lithium methoxide. Alternatively, methanol may be employed in the presence of a strong base such as sodium hydride or lithium di-isopropylamide.

A preferred source of methoxide ions is lithium methoxide. If sodium methoxide is employed, it is also advantageous to employ a small amount of lithium chloride.

The compound of formula (VI) may be present in the form of a disalt i.e. $R^x$ represents a salting ion. Suitable salting ions include sodium, potassium, lithium, calcium, aluminium, magnesium,and dicyclohexylamine, preferably the di-sodium salt. Alternatively the di-acid corresponding to compound (VI), i.e. $R^x$=H, may be employed, or a mono salt thereof together with an additional 2 or 1 equivalent respectively of methoxide, as that amount is initially consumed as a base to produce the disalt (VI).

In the methoxylation aspect of this invention, i.e. the formation of compound (V) from (VI), it is convenient to employ methanol as a solvent. Preferred solvents for this aspect of the invention include dimethylformamide and methanol, in particular a mixture of the two, optionally in the presence of tetrahydrofuran or methyl acetate. A preferred solvent system is dimethylformamide/methanol/methyl acetate. Preferred proportions of dimethylformamide to methanol are from 3:1 to 6:1, preferably 5:1.

The starting material of formula (VI) is preferably present at a concentration of 5–7% of the reaction solution.

For the preparation of compounds of formula (V), a suitable temperature is from −100° C. to −50° C., advantageously from −80° C. to −60° C.

When such low temperature reactions are carried out, it is preferable to pre-cool the solutions of reagents before they added to the reaction mixture. A preferred reaction time is from 5 to 15 minutes.

The following examples illustrate the process of this invention.

EXAMPLE 1

Preparation of disodium 6β-[2-carboxy-2-(thien-3-yl)acetamido]-6α-methoxy penicillanate (temocillin) from disodium 6β-[2-carboxy-2-(thien-3-yl)acetamido] penicillinate (ticarcillin)

0.03 Moles of ticarcillin disodium salt were dissolved in a mixture of dimethylformamide and methanol (160 ml: 25 ml) maintained at 3° to 5° C. The solution was then cooled to −75° C.

0.045 Moles of lithium methoxide were dissolved in 20 ml of methanol. The solution was then cooled to −75° C.

The solution of lithium methoxide was added quickly to the solution of ticarcillin with stirring. The vessel having contained the lithium methoxide solution was washed with 5 ml of methanol and transferred to the reaction vessel.

The reaction mixture was stirred for 1 minute and then 5.5 ml of t-butylhypochlorite, precooled at −75<C were added. The reaction mixture was allowed to stir for about 5 minutes. The reaction was then quenched by the addition of 0.8 ml of concentrated sulfuric acid. The solution temperature was allowed to raise to ambient temperature.

1 liter of methylisobutylketone was added.

The reaction mixture was stirred for about 20 minutes and then filtered under vacuum. The crude product was washed with 50 ml of methylisobutylketone followed by 50 ml of diisopropylether. The crude product was redissolved in 50 ml of distilled water. The organic layer was separated and discarded, and the aqueous solution acidified to pH 2 with 5N hydrochloric acid in the presence of 50 ml of methylisobutylketone. The aqueous layer was separated and discarded. The organic layer was extracted with 25 ml water and 5N sodium carbonate solution to pH 6.5. The organic layer was separated and the carbonate extract washed with 50 ml of isopropylether. The aqueous solution was degassed and freeze-dried to provide about 9 g of powder containing 81% of temocillin as free acid.

EXAMPLE 2

Preparation of temocillin from disodium ticarcillin 173 g of ticarcillin disodium salt (100% as free acid) was dissolved in a mixture of 375 ml of methyl acetate, 1200 ml of dimethylformamide and 400 ml methanol.

7.5 g lithium chloride were added to the solution. The mixture was cooled to −7<C.

825 ml of methyl acetate, pre-cooled at −75<C, were added. A solution of 36.45 g sodium methoxide in 300 ml methanol was cooled to −75<C and added. After 1 minute, 95 ml of t-butyl hypochlorite were added over a period of 7 minutes. The mixture was stirred for 2.5 hours, maintaining a constant temperature of −75<C.

The reaction was quenched by addition of 15 ml of glacial acetic acid and then 60 ml of triethylphosphite. The product was isolated as described in Example 1 to give 95.5 g temocillin at 82% purity (as free acid).

EXAMPLE 3

Preparation of disodium 6β[2-carboxy-2-(thien-3-yl)acetamido]-6α-methoxy penicillanate (temocillin) from monosodium 6β-[2-carboxy-2-(thien-3-yl)acetamido] penicillanate 0.03 Moles of ticarcillin monosodium salt were dissolved in a mixture of dimethylformamide and methanol (50 ml: 25 ml) maintained at 3° to 5° C. 0.5 g lithium chloride were added to the solution. The solution was then cooled to −75° C. 100 Ml of methylacetate at −70° C. were added to the solution. 0.075 Moles of sodium methoxide were dissolved in 25 ml of methanol. 75 ml of dimethylformamide were added to the solution of sodium methoxide, this solution was cooled to −75° C. and quickly added to the solution of ticarcillin with stirring.

The reaction mixture was stirred for 1 minute and 5.5 ml of precooled (at −75°) t-butylhypochlorite in 75 ml dimethylformamide were added in 5 minutes with good stirring. The reaction mixture was allowed to stir for about 15 minutes and then quenched by the addition of 1 ml of glacial acetic acid. The solution temperature was allowed to raise to ambient temperature. The product was isolated as described in Example 1.

EXAMPLE 4
Preparation of temocillin from monosodium ticarcillin 11.5 g of monosodium ticarcillin (100% as pfa) was dissolved in a mixture of 38 ml dimethyl formamide and 30 ml methanol. To this solution was added 0.5 g of lithium chloride, the solution cooled to −75° C. and then 115 ml of methyl acetate, precooled to −75° C., were added. Then a solution of 4.75 g of sodium methoxide in 25 ml methanol was prepared and when dissolved 85 ml of DMF, precooled to −75° C., is added thereto. This solution was then added to the ticarcillin solution. Immediately thereafter a solution of 4.95 ml of t-butyl hypochlorite diluted with 75 ml of dimethylformamide pre cooled to −75°, was added. After 15 mins, 1.6 ml of glacial acetic acid were added, and after 1 minute, 2 ml of triethyl phosphite.

The product was isolated as described in Example 1, to give 8 g product (purity 82% as pfa).

EXAMPLE 5
Preparation of disodium 6β[2-carboxy-2-phenylacetamido] 6α-methoxy penicillanate from disodium 6β-[2-carboxy-2-phenylacetamido]penicillanate (carbenicillin)

0.06 Moles of carbenicillin disodium salt were dissolved in a mixture of dimethylformamide and methanol (100 ml: 50 ml) maintained at 3° to 5° C. The solution was then cooled to −75° C. and additional quantity of dimethylformamide (220 ml) was then added. 0.09 Moles of lithium methoxide were added quickly to the solution of carbencillin with stirring. The vessel having contained the lithium methoxide solution was washed with 5 ml of methanol and transferred to the reaction vessel.

The reaction mixture was stirred for 1 minute and then 11 ml of precooled (at −75° C.) t-butylhypochlorite (0.092 moles) were added. The reaction mixture was allowed to stir for about 15 minutes, and then quenched by the addition of 1.6 ml of concentrated sulfuric acid. The solution temperature was allowed to raise to ambient temperature. The product was isolated as described in example 1.

We claim:

1. A process for the preparation of an antibacterially active β-lactam compound of the formula (III):

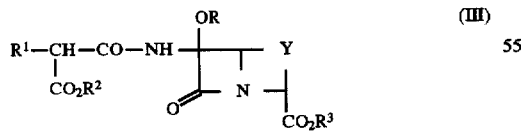

a salt thereof, or an ester thereof wherein R is alkyl of 1 to 6 carbon atoms, $R^1$ is a hydrocarbon or heterocyclyl group; $R^2$ is hydrogen or a pharmaceutically acceptable salt or ester, $R^3$ is hydrogen or a pharmaceutically acceptable salt or in vivo hydrolysable ester, and Y is —S—C(CH$_3$)$_2$—, —S—CH$_2$, or —Y$^1$—CH$_2$—C(Z)=, wherein Y$^1$ is oxygen, sulphur or —CH$_2$— and Z is hydrogen, halo, alkoxy of 1 to 6 carbon atoms, —CH$_2$Q or —CH=CH—Q wherein Q is hydrogen, halo, hydroxy, mercapto, cyano, pyridinium, carboxy or an ester thereof, alkoxy of 1 to 6 carbon atoms, acyloxy, aryl, heterocyclyl or heterocyclylthio which process comprises reacting a compound of formula (IV):

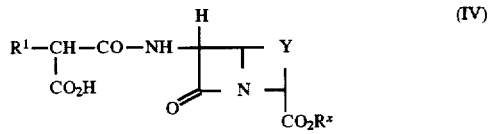

where $R^1$, and Y are as above defined and $R^x$ is hydrogen or a carboxyl blocking group, with a halogenating agent in the presence of an alkali metal alkoxide having an alkoxide group of formula —OR where R is alkyl of 1 to 6 carbon atoms whereby said alkali metal alkoxide acts both, (a) as a strong base to facilitate the action of said halogenating agent to produce an intermediate acylimine derivative of the compound of formula IV, and (b) as a source of the ion RO⁻ where R is alkyl of 1 to 6 carbon atoms for in situ reaction with said intermediate, thereby to form said compound of formula III, and optionally thereafter converting the β-lactam produced to a salt or ester thereof.

2. A process according to claim 1 wherein Y is —S—C(CH$_3$)$_2$—.

3. A process according to claim 1 wherein the alkali metal alkoxide is lithium alkoxide.

4. A process according to claim 1 wherein the alkali metal alkoxide is sodium alkoxide in admixture with lithium chloride.

5. A process for the preparation of an antibacterially active β-lactam compound of the formula (III):

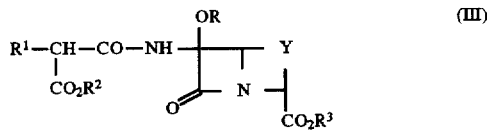

a salt thereof, or an ester thereof wherein R is methyl; $R^1$ is phenyl, p-hydroxyphenyl, 3,4-dihydroxyphenyl or 2- or 3- thienyl; $R^2$ is hydrogen or a pharmaceutically acceptable salt or ester, $R^3$ is hydrogen or a pharmaceutically acceptable salt or in vivo hydrolysable ester, and Y is —S—C(CH$_3$)$_2$—, which process comprises reacting a compound of formula (IV):

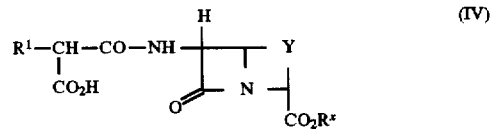

where $R^1$, and Y are as above defined and $R^x$ is hydrogen or a carboxyl blocking group, with a halogenating agent in the presence of an alkali metal methoxide whereby said alkali metal methoxide acts both, (a) as a strong base to facilitate the action of said halogenating agent to produce an intermediate acylimine derivative of the compound of formula IV, and (b) as a source of the methoxide ion for in situ reaction with said intermediate, thereby to form said compound of formula III, and optionally thereafter converting the β-lactam produced to a salt or ester thereof.

6. A process for the preparation of an antibacterially active β-lactam of the formula (V):

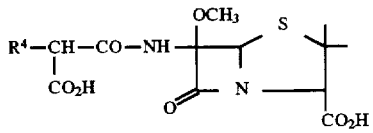

(V)

or a pharmaceutically acceptable salt thereof wherein $R^4$ is phenyl, p-hydroxyphenyl or 2- or 3-thienyl which process comprises reacting a salt of a compound of the formula (VI):

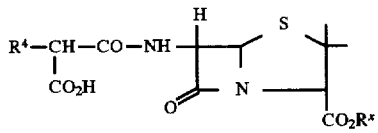

(VI)

wherein $R^4$ is as above defined and $R^x$ is a carboxy-blocking group with a halogenating agent in the presence of an alkali metal methoxide which acts both, (a) as a strong base to facilitate the action of said halogenating agent to produce an intermediate acylimine derivative of the compound of formula (VI) and (b) as a source of the methoxide ion for in situ reaction with said intermediate, thereby to form said compound of formula (V), and if $R^x$ is other than a salt moiety, converting the group —$CO_2R^x$ to a free acid or salt.

7. A process according to claim 6 wherein the source of methoxide ions is lithium methoxide.

8. A process according to claim 6 wherein the compound of formula (VI) is in the form of a mono- or di-alkali metal salt.

9. A process according to claim 6, wherein the source of methoxide ions is sodium methoxide.

10. A process according to claim 6, wherein the source of methoxide ions is sodium methoxide in admixture with lithium chloride.

* * * * *